United States Patent [19]
Steiner et al.

[11] Patent Number: 6,159,962
[45] Date of Patent: Dec. 12, 2000

[54] 3-SUBSTITUTED 3,4-DIHYDRO-THIENO[2,3-D]PYRIMIDINE DERIVATIVES AND PRODUCTION AND USE OF THE SAME

[75] Inventors: Gerd Steiner, Kirchheim; Uta Dullweber, Frankenthal; Dorothea Starck, Ludwigshafen; Alfred Bach, Heidelberg; Karsten Wicke, Altrip; Hans-Jürgen Teschendorf, Dudenhofen; Francisco-Javier Garcia-Ladona, Kandel; Franz Emling, Ludwigshafen, all of Germany

[73] Assignee: BASF Aktiengesellschaft, Ludwigshafen, Germany

[21] Appl. No.: 09/445,222

[22] PCT Filed: May 29, 1998

[86] PCT No.: PCT/EP98/03230

§ 371 Date: Dec. 6, 1999

§ 102(e) Date: Dec. 6, 1999

[87] PCT Pub. No.: WO98/56792

PCT Pub. Date: Dec. 17, 1998

[30] Foreign Application Priority Data

Jun. 13, 1997 [DE] Germany ............ 197 24 980

[51] Int. Cl.[7] ............ C07D 417/06; C07D 417/14; A61K 31/551; A61K 31/559; A61P 25/24
[52] U.S. Cl. ............ 514/211.08; 514/217.06; 514/252.11; 514/252.16; 514/258; 540/575; 540/600; 544/278
[58] Field of Search ............ 544/278; 540/575, 540/600; 514/258, 211.08, 217.06, 252.11, 252.16

[56] References Cited

U.S. PATENT DOCUMENTS 4,835,157 5/1989 Press et al. ............ 514/258

FOREIGN PATENT DOCUMENTS

98/11110 3/1998 WIPO.

OTHER PUBLICATIONS

Monatshefte fur Chem. 106, 111–116 (1975) Sauter et al.
Neuropharmacology vol. 33, 3/4, 393–402, 1994 Starkey et al.
BASF patent application OZ47291 1–35.
2–Amino–Thiophene aus . . . Gewald et al., 94–100.
Subclassification of presynaptic . . . , Fink et al., Springer–Verlag 1995, 451–454
Neuropharmacology vol. 34, No. 4, 383–392, 1995 Hutson et al.
Neuropharmacology vol. 34, No. 4, 393–403 1995, Johansson et al.
Behavioural Brain Res. 73 (1996) 79–82, Price et al.
Neuropharmacology vol. 34, No. 4, 377–382, 1995, Skingle et al.

Primary Examiner—Mukund J. Shah
Assistant Examiner—Thomas McKenzie
Attorney, Agent, or Firm—Keil & Weinkauf

[57] ABSTRACT

3-Substituted 3,4-dihydrothieno[2,3-d]pyrimidine derivatives of the formula I

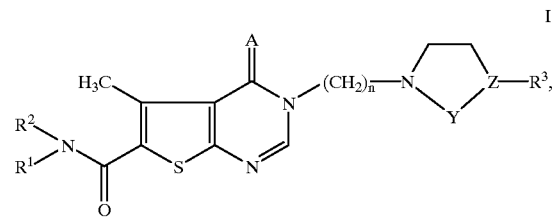

where $R^1$ and $R^2$ are a hydrogen atom or a $C_1$–$C_4$-alkyl group, $R^3$ is a phenyl, pyridyl, pyrimidinyl or pyrazinyl group which is unsubstituted or mono- or disubstituted by halogen atoms, $C_1$–$C_4$-alkyl, trifluoromethyl, trifluoromethoxy, hydroxyl, $C_1$–$C_4$-alkoxy, amino, monomethylamino, dimethylamino, cyano or nitro groups and which may be fused to a benzene nucleus which may be unsubstituted or mono- or disubstituted by halogen atoms, $C_1$–$C_4$-alkyl, hydroxyl, trifluoromethyl, $C_1$–$C_4$-alkoxy, amino, cyano or nitro groups, and may contain 1 nitrogen atom, or to a 5- or 6-membered ring, which may contain 1–2 oxygen atoms, A is NH or an oxygen atom, Y is $CH_2$, $CH_2$—$CH_2$, $CH_2$—$CH_2$—$CH_2$ or $CH_2$—CH, Z is a nitrogen atom, carbon atom or CH, it being possible for the linkage between Y and Z also to be a double bond, and n is 2, 3 or 4, and the physiologically tolerated salts thereof.

6 Claims, No Drawings

3-SUBSTITUTED 3,4-DIHYDRO-THIENO[2,3-D]PYRIMIDINE DERIVATIVES AND PRODUCTION AND USE OF THE SAME

This application is the National Stage Application of PCT/EP98/03230, which claims priority from German Application 19724980.9 filed Jun. 13, 1997, and is filed under 37 CFR 1.78.

The invention relates to novel 3,4-dihydrothieno[2,3-d] pyrimidine derivatives, their preparation and use for producing active ingredients for drugs.

Classical antidepressants, and the newer selective serotonin reuptake inhibitors (SSRIs), develop their antidepressant effect inter alia by inhibiting active reuptake of the transmitter into the presynaptic nerve endings. Unfortunately, the antidepressant effect thereof does not have its onset until treatment has lasted at least 3 weeks, and, moreover, about 30% of patients are therapy-resistant.

Blockade of presynaptic serotonin autoreceptors increases, by abolishing negative coupling, the serotonin release and thus the current transmitter concentration in the synaptic cleft. This increase in the transmitter concentration is regarded as the principle of the antidepressant effect. This mechanism of action differs from previously known antidepressants which activate both the presynaptic and somatodendritic autoreceptors and therefore result in a delayed onset of action, only after desensitization of these autoreceptors. Direct autoreceptor blockade bypasses this effect.

According to current knowledge, the presynaptic serotonin autoreceptor is of the $5\text{-HT}_{1B}$ subtype (Fink et al., Arch. Pharmacol. 352 (1995), 451). Selective blockade thereof by $5\text{-HT}_{1B/D}$ antagonists increases serotonin release in the brain: G. W. Price et al., Behavioural Brain Research 73 (1996), 79–82; P. H. Hutson et al., Neuropharmacology Vol. 34, No. 4 (1995), 383–392.

However, surprisingly, the selective $5\text{-HT}_{1B}$ antagonist GR 127 935 reduces serotonin release in the cortex after systemic administration. One explanation might be stimulation of somatodendritic $5\text{-HT}_{1A}$ receptors in the raphe region by the released serotonin, which inhibits the firing rate of serotonergic neurons and thus serotonin release (M. Skingle et al., Neuropharmacology Vol. 34 No. 4 (1995), 377–382, 393–402).

One strategy for bypassing the autoinhibitory effects in serotonergic areas of origin thus aims at blockade of presynaptic $5\text{-HT}_{1B}$ receptors. This hypothesis is supported by the observation that the effect of paroxetine on serotonin release in the dorsal raphe nucleus of the rat is potentiated by the $5\text{-HT}_{1B}$ receptor antagonist GR 127 935 (Davidson and Stamford, Neuroscience Letts., 188 (1995),41).

The second strategy includes blockade of both types of autoreceptors, namely the $5\text{-HT}_{1A}$ receptors, in order to intensify neuronal firing, and the $5\text{-HT}_{1B}$ receptors, in order to increase terminal serotonin release (Starkey and Skingle, Neuropharmacology 33 (3–4) (1994),393).

$5\text{-HT}_{1B/D}$ antagonists, alone or coupled to a $5\text{-HT}_{1A}$ receptor antagonistic component, should therefore cause a greater increase in serotonin release in the brain and might therefore be associated with advantages in the therapy of depressions and related psychological disorders.

It has now been found that 3-substituted 3,4-dihydrothieno-[2,3-d]pyrimidine derivatives of the formula I

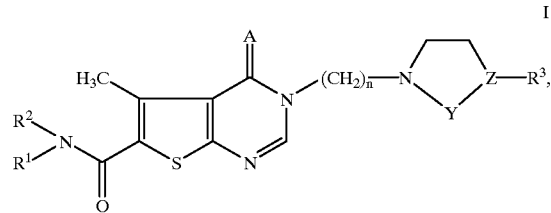

where
$R^1$ and $R^2$ are a hydrogen atom or a $C_1\text{-}C_4$-alkyl group,
$R^3$ is a phenyl, pyridyl, pyrimidinyl or pyrazinyl group which is unsubstituted or mono- or disubstituted by halogen atoms, $C_1\text{-}C_4$-alkyl, trifluoromethyl, trifluoromethoxy, hydroxyl, $C_1\text{-}C_4$-alkoxy, amino, monomethylamino, dimethylamino, cyano or nitro groups and which may be fused to a benzene nucleus which may be unsubstituted or mono- or disubstituted by halogen atoms, $C_1\text{-}C_4$-alkyl, hydroxyl, trifluoromethyl, $C_1\text{-}C_4$-alkoxy, amino, cyano or nitro groups, and may contain 1 nitrogen atom, or to a 5- or 6-membered ring, which may contain 1–2 oxygen atoms,
A is NH or an oxygen atom,
Y is $CH_2$, $CH_2\text{---}CH_2$, $CH_2\text{---}CH_2\text{---}CH_2$ or $CH_2\text{---}CH$,
Z is a nitrogen atom, carbon atom or CH, it being possible for the linkage between Y and Z also to be a double bond,
and n is 2, 3 or 4,
and the salts thereof with physiologically tolerated acids, have valuable pharmacological properties.
Particularly preferred compounds are those where
$R_1$ and $R^2$ are methyl
$R^3$ is o-methoxyphenyl, 1-naphthyl, 2-methoxy-1-naphthyl, 2-methyl-1-naphthyl
A is an oxygen atom
Y is $CH_2\text{---}CH_2$
Z is a nitrogen atom
and n is 2 and 3.

The novel compounds of the formula I can be prepared by reacting a compound of the formula II

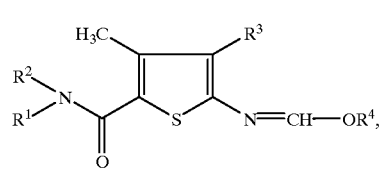

where $R_1$ [sic] has the abovementioned meaning, $R^3$ is a cyano group or a $C_{1\text{-}3}$-alkylcarboxylic ester group, and $R^4$ is $C_{1\text{-}3}$-alkyl, with a primary amine of the formula III

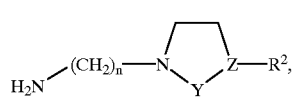

where $R^3$ [sic] has the abovementioned meaning, and converting the compound obtained in this way where appropriate into the addition salt of a physiologically tolerated acid.

The reaction is expediently carried out in an inert organic solvent, in particular a lower alcohol, eg. methanol or ethanol, or a cyclic saturated ether, in particular tetrahydrofuran or dioxane.

The reaction is, as a rule, carried out at from 20 to 110° C., in particular from 60 to 90° C., and is generally complete within 1 to 10 hours.

Alternatively, a compound of the formula II

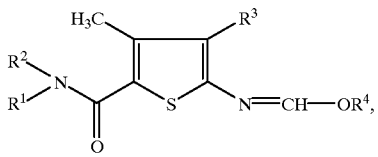

where $R_1$ [sic] has the abovementioned meaning, $R^3$ is a cyano group or a $C_{1-3}$-alkylcarboxylic ester group, and $R^4$ is $C_{1-3}$-alkyl, is reacted with a primary amino alcohol of the formula IV

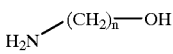

in an inert solvent, preferably alcohols such as ethanol, at from 60° to 120° C., to give the cyclization product V (X=OH)

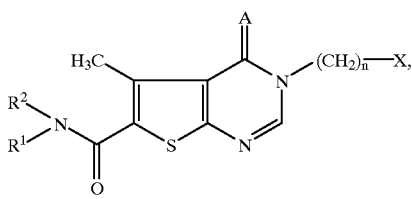

which is subsequently converted with a halogenating agent, eg. thionyl chloride or hydrobromic acid, in an organic solvent such as a halohydrocarbon or without solvent at from room temperature to 100° C. into the corresponding halogen derivative V (X=Cl, Br).

Finally, the halogen derivative of the formula V (X=Cl, Br) is reacted with an amine of the formula VI

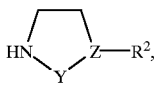

where Y, Z and $R^2$ have the abovementioned meanings, to give the novel final product of the formula I. This reaction takes place best in an inert organic solvent, preferably toluene or xylene, in the presence of a base, eg. potassium carbonate or potassium hydroxide, at from 60° C. to 150° C.

The novel compounds of the formula I can be either recrystallized by recrystallization from conventional organic solvents, preferably from a lower alcohol such as ethanol, or purified by column chromatography.

The free 3-substituted pyrido[3',4':4,5]thieno[2,3-d] pyrimidine derivatives of the formula I can [lacuna] in a conventional way into the acid addition salts of [sic] a solution with the stoichiometric amount of the appropriate acid. Examples of pharmaceutically acceptable acids are hydrochloric acid, phosphoric acid, sulfuric acid, methanesulfonic acid, sulfamic acid, maleic acid, fumaric acid, oxalic acid, tartaric acid or citric acid.

The invention accordingly also relates to a therapeutic composition having a content of a compound of the formula I or its pharmacologically acceptable acid addition salt as active ingredient besides conventional carriers and diluents, and to the use of the novel compounds for controlling diseases.

The novel compounds can be administered orally or parenterally, intravenously or intramuscularly, in a conventional way.

The dosage depends on the age, condition and weight of the patient and on the mode of administration. As a rule, the daily dose of active ingredient is from about 1 to 100 mg/kg of body weight on oral administration and from 0.1 to 10 mg/kg of body weight on parenteral administration.

The novel compounds can be used in conventional solid or liquid pharmaceutical forms, eg. as uncoated or (film-) coated tablets, capsules, powders, granules, suppositories, solutions, ointments, creams or sprays. These are produced in a conventional way. The active ingredients can for this purpose be processed with conventional pharmaceutical aids such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1978). The administration forms obtained in this way normally contain from 1 to 99% by weight of active ingredient.

The substances of the formula II to VI required as starting materials for synthesizing the novel compounds are known or can be synthesized from similar starting materials by preparation methods described in the literature (F. Sauter and P. Stanetty, Monatsh. Chem. 106(5), (1975), 1111–1116; K. Gewald et al., Chem. Ber. 99, (1966) 94–100, German Patent Application 196 36769.7).

The novel compounds have a high affinity for 5-$HT_{1B}$, 5-$HT_{1D}$ and 5-$HT_{1A}$ serotonin receptors. The affinity for these receptors is moreover about the same, at least of the same order of magnitude. Furthermore, some of the novel compounds show good serotonin reuptake inhibition, a principle which is implemented in most antidepressants.

These compounds are suitable as drugs for treating pathological states in which the serotonin concentration is reduced and in which, as part of therapy, it is wished to block specifically the activity of the presynaptic 5-$HT_{1B}$, 5-$HT_{1A}$, 5-$HT_{1D}$ receptors without having a great effect on other receptors too. An example of a pathological state of this type is depression.

The compounds of the present invention may also be useful for treating mood disorders with a central nervous causation, such as seasonal affective disorders and dysthymia. These also include anxiety states such as generalized anxiety, panic attacks, sociophobia, obsessive-compulsive neuroses and post-traumatic stress symptoms, memory disturbances including dementia, amnesias and age-related memory loss, and psychogenic eating disorders such as anorexia nervosa and bulimia nervosa.

The novel compounds can additionally be useful for treating endocrine disorders such as hyperprolactinemia and for treating vasospasms (especially of the cerebral vessels), hypertension and gastrointestinal disorders associated with motility and secretion disturbances. Another area of use is for sexual disorders.

The following examples serve to illustrate the invention:

A Preparation of the Starting Materials a) 2-Amino-3-carboethoxy-5-methyl-5-dimethylcarbamoylthiophene 82.8 ml, (775 mM [sic]) of ethyl cyanoacetate and 24.8 g (755 mM [sic]) of sulfur powder were added to 100 g (775 mM [sic]) of N,N-dimethylacetoacetamide in 400 ml of ethanol and then, while stirring vigorously and under a nitrogen atmosphere, 90 ml (647 mM [sic]) of triethylamine were added dropwise. After 1 h, the mixture was refluxed for 8 h and then left to stir at room temperature overnight. The mixture was concentrated under reduced pressure, the residue was taken up in 2 l of water, the pH was adjusted to 9, and two extractions with methylene chloride were carried out. The organic phase was dried and concentrated and then the crude product (70 g) was purified by dissolving in 200 ml of boiling ethyl acetate. The solid which precipitated on stirring overnight was, after cooling in an ice bath, filtered off with suction and washed several times with cold ethyl acetate. 39.0 g (20%) of product were isolated as a gray solid of melting point 122–124° C.

b) 2-Ethoxymethyleneamino-3-carboethoxy-4-methyl-5-dimethylcarbamoylthiophene 2.0 ml of acetic anhydride were added to 30.6 g (119 mM [sic]) of 2-amino-3-carboethoxy-4-methyl-5-dimethylcarbamoylthiophene in 150 ml of triethyl orthoformate and refluxed under nitrogen for 2 h. The mixture was then completely evaporated in a rotary evaporator at 80° C. 35.6 g (96%) of crude product were isolated as a dark oil which is sufficiently pure for the next reaction.

c) 3-(2-Hydroxyethyl)-5-methyl-6-dimethylcarbamoylthieno[2,3-d]pyrimidin-4-one 8.0 ml (133 mM [sic]) of ethanolamine were added to 35.6 g (114 mM [sic]) of 2-ethoxymethyleneamino-3-carboethoxy-5-methyl-5-dimethylcarbamoylthiophene [sic] in 200 ml of ethanol and refluxed for 2 h. The mixture was then concentrated under reduced pressure. 29.9 g (93%) of dark viscous oil were isolated.

d) 3-(2-Chloroethyl)-5-methyl-6-dimethylcarbamoylthieno[2,3-d]pyrimidin-4-one 29.9 g (106 mM [sic]) of 3-(2-hydroxyethyl)-5-methyl-6-dimethylcarbamoylthieno [2,3-d]pyrimidin-4-one in 200 ml of 1,2-dichloroethane were heated to reflux (slow dissolution) and then 12.7 ml (175 mM [sic]) of thionyl chloride in 20 ml of 1,2-dichloroethane were added dropwise. After refluxing for 1 h, the reaction mixture was cooled and concentrated. The crude product was partitioned between methylene chloride and water at pH=9. Drying and concentration of the organic phase resulted in isolation of 44.1 g (83%) of product as a dark oil which was purified by column chromatography (silica gel, eluent ethyl acetate). 23.8 g (76%) of product were isolated with melting point 120–122° C.

Other $C_1$–$C_4$-mono- or dialkylcarbamoyl derivatives of formula II and V can be prepared as in methods a) to d).

e) N-(1-Naphthyl)piperazine 83.2 g (966 mM [sic]) of piperazine, 38.0 g (339 mM [sic]) of potassium tert-butoxide and 50.0 g (241 mM [sic]) of 1-bromonaphthalene were added to a mixture of 5.4 g (24.2 mM [sic]) of palladium acetate and 14.7 g (48.3 mM [sic]) of tri-o-tolylphosphine in 500 ml of xylene, and the mixture was refluxed while stirring vigorously under a nitrogen atmosphere for 10 h. The mixture was then diluted with methylene chloride, the insoluble residues were filtered off, and the filtrate was concentrated. The crude product was purified by column chromatography (silica gel, eluent THF/methanol/ammonia 85/13/2). 21.5 g (42%) of product were isolated with melting point 84–86° C.

f) N-(2-Methyl-1-naphthyl)piperazine 14.7 g (82.7 mM [sic]) of bis(2-chloroethyl)amine ×HCl were added to 13.0 g (82.7 mM [sic]) of 1-amino-2-methylnaphthalene in 100 ml of chlorobenzene and refluxed under nitrogen for 90 h. The mixture was then concentrated and partitioned between methylene chloride and water at pH=9, and the organic phase was dried and concentrated. The crude product was purified by column chromatography (silica gel, eluent/THF/methanol/ammonia 85/13/2. 11.6 g (62%) of product were isolated.

g) 4-Piperazin-1-ylisoquinoline 4.51 g (21.7 mM [sic]) of 4-bromoisoquinoline, 4.65 g (25.0 mM [sic]) of t-butyl piperazine-N-carboxylate, 0.1 g (0.11 mM [sic]) of tris(dibenzylideneacetone)dipalladium, 0.11 g (0.18 mM [sic]) of 2,2'-bis(diphenylphosphino)-1,1'-binaphthyl and 2.92 g (30.4 mM [sic]) of sodium t-butoxide were mixed in 50 ml of toluene and stirred at 75° C. for 2 h. The reaction mixture was added to ice/sodium chloride and extracted with ethyl acetate, the organic phase was dried over sodium sulfate and the solvent was removed in a rotary evaporator. The product crystallized out and was filtered off with suction and washed with pentane. 5.5 g (81%) of the Boc-protected piperazine (melting point: 111° C.) were obtained. 5.2 g (16.6 mM [sic]) of this substance were taken up in 17 ml of dichloromethane and, at 0° C., taken up slowly in 17 ml of dichloromethane [sic], and, at 0° C., 17 ml (0.22 mM [sic]) of trifluoroacetic acid were slowly added. The mixture was left to stir at 0° C. for 4 h, poured into ice-water and extracted with dichloromethane. The aqueous phase was filtered, made alkaline and extracted with dichloromethane. Drying over sodium sulfate and substantial removal of the solvent were followed by dilution with diethyl ether and precipitation of the hydrochloride with ethereal hydrochloric acid. 3.2 g (67%) of the product were obtained with melting point 293–294° C.

Further piperazine derivatives (see Examples) not disclosed in the literature (cf. also German Patent Application 19636769.7) were prepared as in e), f) and g).

B Preparation of the Final Products

EXAMPLE 1

3,4-Dihydro-5-methyl-6-dimethylcarbamoyl-3-[2-(4-(2-methoxy-phenyl)-1-piperazinyl) ethyl]thieno(2,3-d]pyrimidin-4-one [sic]

1.9 g (8.0 mM [sic]) of 1-(2-aminoethyl)-4-(2-methoxyphenyl)-piperazine were added to 2.4 g (7.8 mM [sic]) of 2-ethoxymethyleneamino-3-carboethoxy-4-methyl-5-dimethylcarbamoyl thiophene in 30 ml of ethanol and refluxed for 2 h. The product crystallized out after standing overnight and was filtered off with suction and washed with a little ethanol. 2.2 g (62%) of product were isolated with melting point 188–190° C.

EXAMPLE 2

3,4-Dihydro-5-methyl-6-dimethylcarbamoyl-3-[2-(4-(2,3-dimethyl-phenyl)-1-piperazinyl)ethy 1.1 g (5.0 mM [sic]) of 1-(2,3-dimethylphenyl)piperazine hydrochloride and 1.54 ml (11 mM [sic]) of triethylamine were added to 1.5 g (5.0 mM [sic]) of 3-(2-chloroethyl)-5-methyl-6-dimethylcarbamoylthieno[2,3-d]pyrimidin-4-one in 15 ml of dimethylformamide and heated at 125° C. under nitrogen for a total of 3 h. Pouring into water was followed by extraction with ethyl acetate, the organic phase was extracted with dilute hydrochloric acid at pH=2, and the aqueous phase resulting from this was made basic with dilute sodium hydroxide solution. The crude product was extracted with dichloromethane and, after drying over sodium sulfate, the solvent was removed under reduced pressure. The oily residue was crystallized from a little methanol and filtered off with suction. It was possible in this way to obtain 0.7 g (31%) of product with melting point 160–161° C.

The following were prepared as in Examples 1 and 2:

3. 3,4-Dihydro-5-methyl-6-dimethylcarbamoyl-3-[2-(4-(1-naphthyl)-1-piperazinyl)ethyl]thieno[2,3-d]pyrimidin-4-one, melting point 190–191° C.
4. 3,4-Dihydro-5-methyl-6-dimethylcarbamoyl-3-[2-(4-(2-methyl-1-napththyl)-1-piperazinyl)ethyl]thieno[2,3-d]pyrimidin-4-one, melting point 178–180° C.
5. 3,4-Dihydro-5-methyl-6-dimethylcarbamoyl-3-[2-(4-(2-methoxy-1-naphthyl)-1-piperazinyl)ethyl]thieno[2,3-d]pyrimidin-4-one×H$_2$O, melting point 153–155° C. (decomposition)
6. 3,4-Dihydro-5-methyl-6-dimethylcarbamoyl-3-[2-(4-(2-methylphenyl)-1-piperazinyl)ethyl]thieno[2,3-d]pyrimidin-4-one
7. 3,4-Dihydro-5-methyl-6-dimethylcarbamoyl-3-[2-(4-(3-tri-fluoromethylphenyl)-1-piperazinyl)ethyl]thieno[2,3-d]-pyrimidin-4-one, melting point 146° C.
8. 3,4-Dihydro-5-methyl-6-dimethylcarbamoyl-3-[2-(4-(2-chloro-phenyl)-1-piperazinyl)ethyl]thieno[2,3-d]pyrimidin-4-one,
9. 3,4-Dihydro-5-methyl-6-dimethylcarbamoyl-3-[2-(4-pyrimidin-2-ylpiperazin-1-yl)ethyl]thieno[2,3-d]pyrimidin-4-one×2HCl×4 H$_2$O, melting point 180–182° C. (decomposition)
10. 3,4-Dihydro-5-methyl-6-dimethylcarbamoyl-3-[2-(4-pyridin-2-ylpiperazin-1-yl)ethyl]thieno[2,3-d]pyrimidin-4-one
11. 3,4-Dihydro-5-methyl-6-dimethylcarbamoyl-3-[2-(4-quinolin-2-ylpiperazin-1-yl)ethyl]thieno[2,3-d]pyrimidin-4-one,
12. 3,4-Dihydro-5-methyl-6-dimethylcarbamoyl-3-[2-(4-(3,5-dichlorophenyl)-1-piperazinyl)ethyl]thieno[2,3-d]pyrimidin-4-one
13. 3,4-Dihydro-5-methyl-6-dimethylcarbamoyl-3-[2-(4-tetralin-5-ylpiperazin-1-yl)ethyl]thieno[2,3-d]pyrimidin-4-one, melting point 174° C.
14. 3,4-Dihydro-5-methyl-6-dimethylcarbamoyl-3-[2-(4-indan-4-ylpiperazin-1-yl)ethyl]thieno[2,3-d]pyrimidin-4-one, melting point 153° C.
15. 3,4-Dihydro-5-methyl-6-dimethylcarbamoyl-3-[2-(4-(2-cyanophenyl)-1-piperazinyl)ethyl]thieno[2,3-d]pyrimidin-4-one, melting point 210° C. (hydrochloride)
16. 3,4-Dihydro-5-methyl-6-dimethylcarbamoyl-3-[2-(4-isoquinolin-4-ylpiperazin-1-yl)ethyl]thieno[2,3-d]pyrimidin-4-one
17. 3,4-Dihydro-5-methyl-6-dimethylcarbamoyl-3-[3-(4-pyrimidin-2-ylpiperazin-1-yl)propyl]thieno[2,3-d]pyrimidin-4-one, ×2 HCl×2 H$_2$O, melting point 209–211° C. (decomposition)
18. 3,4-Dihydro-5-methyl-6-dimethylcarbamoyl-3-[2-(4-(2-methoxyphenyl)-1-piperidinyl)ethyl]thieno[2,3-d]pyrimidin-4-one
19. 3,4-Dihydro-5-methyl-6-dimethylcarbamoyl-3-[2-(4-(2-methoxyphenyl)-3,4-dihydro-1-piperidinyl)ethyl]thieno[2,3-d]-pyrimidin-4-one [sic]
20. 3,4-Dihydro-5-methyl-6-dimethylcarbamoyl-3-[2-(4-naphth-1-ylpiperidin-1-yl)ethyl]thieno[2,3-d]pyrimidin-4-one
21. 3,4-Dihydro-5-methyl-6-dimethylcarbamoyl-3-[2-(4-(2-methoxy-1-naphthyl)-3,4-dehydro-1-piperidinyl)ethyl]thieno-[2,3-d]pyrimidin-4-one
22. 3,4-Dihydro-5-methyl-6-dimethylcarbamoyl-3-[2-(4-naphth-1-yl-1,4-hexahydro-1,4-diazepin-1-yl)ethyl]thieno-[2,3-d]pyrimidin-4-one, melting point 225–230° C. (hydrochloride)
23. 3,4-Dihydro-5-methyl-6-carbamoyl-3-[2-(4-(1-naphthyl)-1-piperazinyl)ethyl]thieno[2,3-d]pyrimidin-4-one
24. 3,4-Dihydro-5-methyl-6-carbamoyl-3-[2-(4-pyrimidin-2-yl-piperazin-1-yl)ethyl]thieno[2,3-d]pyrimidin-4-one
25. 3,4-Dihydro-5-methyl-6-diethylcarbamoyl-3-[2-(4-(2-methoxyphenyl)-1-piperazinyl)ethyl]thieno[2,3-d]pyrimidin-4-one
26. 3,4-Dihydro-5-methyl-6-diethylcarbamoyl-3-[2-(4-(1-naphthyl)-1-piperazinyl)ethyl]thieno[2,3-d]pyrimidin-4-one
27. 3,4-Dihydro-5-methyl-6-diethylcarbamoyl-3-[2-(4-pyrimidin-2-ylpiperazin-1-yl)ethyl]thieno[2,3-d]pyrimidin-4-one
28. 3,4-Dihydro-5-methyl-6-dimethylcarbamoyl-3-[2-(4-quinazolin-4-ylpiperazin-1-yl)ethyl]thieno[2,3-d]pyrimidin-4-one, melting point 295–300° C. (hydrochloride)
29. 3,4-Dihydro-5-methyl-6-dimethylcarbamoyl-3-[2-(4-(2,4-dimethoxyphenyl)-1-piperazinyl)ethyl]thieno[2,3-d]pyrimidin-4-one, melting point 170–171° C.
30. 3,4-Dihydro-5-methyl-6-dimethylcarbamoyl-3-[2-(4-(2,5-dimethylphenyl)-1-piperazinyl)ethyl]thieno[2,3-d]pyrimidin-4-one, melting point 90–91° C.
31. 3,4-Dihydro-5-methyl-6-dimethylcarbamoyl-3-[2-(4-naphth-1-yl-3,4-dehydro-1-piperidinyl)ethyl]thieno[2,3-d]-pyrimidin-4-one, MS: m$^+$=509.1

We claim:
1. A 3-substituted 3,4-dihydrothieno[2,3d]pyrimidine derivative of the formula I

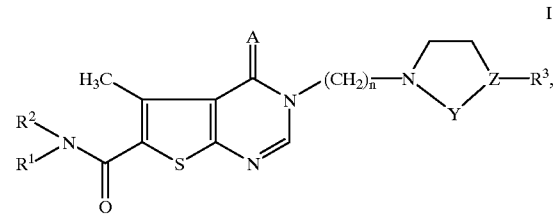

where
R$^1$ and R$^2$ are a hydrogen atom or a C$_1$–C$_4$-alkyl group,
R$^3$ is a phenyl, pyridyl, pyrimidinyl or pyrazinyl group which is unsubstituted or mono- or disubstituted by halogen atoms, C$_1$–C$_4$-alkyl, trifluoromethyl, trifluoromethoxy, hydroxyl, C$_1$–C$_4$-alkoxy, amino, monomethylamino, dimethylamino, cyano or nitro groups and which may be fused to a benzene nucleus which may be unsubstituted or mono- or disubstituted by halogen atoms, C$_1$–C$_4$-alkyl, hydroxyl, trifluoromethyl, C$_1$–C$_4$-alkoxy, amino, cyano or nitro groups, and may contain 1 nitrogen atom, or to a 5- or 6-membered ring, which may contain 1–2 oxygen atoms, A is NH or an oxygen atom, Y is $CH_2$, $CH_2-CH_2$, $CH_2-CH_2-CH_2$ or $CH_2-CH$, Z is a nitrogen atom, carbon atom or CH, or optionally the linkage between Y and Z can be a double bond, or n is 2, 3 or 4, and the physiologically acceptable salts thereof.

2. A compound as claimed in claim 1, wherein $R^1$ and $R^2$ are methyl, $R^3$ is o-methoxyphenyl, 1-naphthyl, 2-methoxy-1-naphthyl, 2-methyl-1-naphthyl A is an oxygen atom Y is $CH_2-CH_2$ Z is a nitrogen atom or n is 2 and 3.

3. A pharmaceutical composition for the treatment of depression and related disorders comprising an effective amount compound of claims 1 or 2.

4. A method for the treatment of depression and related disorders which comprises administering to the patient a composition comprising an effective amount of a compound of claims 1 or 2.

5. The method of claim 4 wherein the compound acts as selective $5HT_{1B}$ and $5HT_{1A}$ antagonist.

6. The method of claim 5 wherein the selective serotonin antagonism is supplemented by inhibition of serotonin uptake.

* * * * *